United States Patent
Crawford et al.

(10) Patent No.: US 10,024,696 B2
(45) Date of Patent: Jul. 17, 2018

(54) HYPER-VELOCITY PENETRATING PROBE FOR SPECTRAL CHARACTERIZATION

(71) Applicant: RAYTHEON COMPANY, Waltham, MA (US)

(72) Inventors: Thomas M. Crawford, Marana, AZ (US); Richard J. Wright, Tucson, AZ (US); James G. Sierchio, Tucson, AZ (US)

(73) Assignee: RAYTHEON COMPANY, Waltham, MA (US)

( * ) Notice: Subject to any disclaimer, the term of this patent is extended or adjusted under 35 U.S.C. 154(b) by 307 days.

(21) Appl. No.: 15/151,666

(22) Filed: May 11, 2016

(65) Prior Publication Data

US 2017/0328742 A1  Nov. 16, 2017

(51) Int. Cl.
*G01D 5/353* (2006.01)
*F42B 30/00* (2006.01)

(52) U.S. Cl.
CPC ........... *G01D 5/353* (2013.01); *F42B 30/006* (2013.01)

(58) Field of Classification Search
CPC ..... G01N 21/65; G01N 21/255; G01J 3/0218; G01J 3/0289; F42B 30/006; G01D 5/353
USPC ................ 250/554, 221, 227.23, 227.18
See application file for complete search history.

(56) References Cited

U.S. PATENT DOCUMENTS

| | | | |
|---|---|---|---|
| 4,020,765 A | 5/1977 | Glass et al. | |
| 4,411,198 A | 10/1983 | Shrader et al. | |
| 5,546,358 A | 8/1996 | Thomson | |
| 8,687,055 B2* | 4/2014 | Margalith | G01J 3/2803 348/91 |
| 2010/0307363 A1 | 12/2010 | Chishinski | |

FOREIGN PATENT DOCUMENTS

WO    2016/196397 A1    12/2016

OTHER PUBLICATIONS

Gorman et al, "Hypervelocity Impact (HVI)," NASA/CR-2007-214885/VOL1, Digital Wave Corporation, Englewood, Colorado, Sep. 2007.
Jackson et al., "Fibre Optic Sensors for High Speed Hypervelocity Impact Studies and Low Velocity Drop Tests," 21st International Conference on Optical Fiber Sensors, Proc. of SPIE vol. 7753, 2011.
Jackson et al., "Fiber Optic Interrogation Systems for Hypervelocity and Low Velocity Impact Studies," Applied Optics Group, School of Physical Sciences, University of Kent, Canterbury, Kent, CT2 7NH, UK, Jun. 10, 2011.

(Continued)

*Primary Examiner* — Que T Le
(74) *Attorney, Agent, or Firm* — Lando & Anastasi, LLP

(57) ABSTRACT

A hyper-velocity impact sensor including an optical fiber probe that transmits an optical pulse generated during impact with an object, a spectroscopic analyzer that receives the optical pulse and produces spectral information about the optical pulse, a connecting optical fiber configured to convey the optical pulse between the optical fiber probe and the spectroscopic analyzer, and at least one processor coupled to the spectroscopic analyzer and configured to receive and analyze the spectral information to determine at least one chemical element or compound contained in the object.

20 Claims, 3 Drawing Sheets

(56) References Cited

OTHER PUBLICATIONS

International Search Report and Written Opinion for application No. PCT/US2017/020918 dated Nov. 2, 2017.
Lawrence et al., "Spectral measurements of hypervelocity impact flash", International Journal of Impact Engineering, vol. 33, pp. 353-363, 2006.
Verreault et al., "Emission Spectroscopy of Hypervelocity Impactson Aluminum, Organic and High-Explosive Targets", Procedia Engineering, vol. 103, pp. 618-627, 2015.

* cited by examiner

HYPER-VELOCITY PENETRATING PROBE FOR SPECTRAL CHARACTERIZATION

BACKGROUND

Shock and impact sensors are devices that detect sudden movements, changes, or severe impacts at a predetermined level and indicate whether that level has been exceeded. Impact sensors are used in applications where it is desirable to know when an impact has occurred. In an ultra-high velocity impact, the relative velocities of the colliding objects can be about 5000 meters per second (m/s) or higher which is about the speed of sound in metal. The speed of sound through the metal construction materials of a projectile limits the propagation speed of the shock wave from an impact through the projectile. An example of an application that uses this ultra-high velocity is an anti-projectile projectile. During the final flight stage of the projectile, high velocities are used to improve the accuracy and the efficacy of a successful engagement. In the case where it is desirable for a projectile to send a notification that it has had an impact, this event must be sensed, analyzed, and transmitted after the impact has occurred, but before the sensor, transmitter, and projectile are destroyed by the impact.

US Patent Pub 2010/0307353 entitled "Ultra-high velocity projectile impact sensor" discloses an apparatus for detecting the impact of an ultra-high velocity projectile using an optical fiber located in the projectile. An optical fiber provides a predictable response under the conditions of an ultra-high velocity projectile impact. When the optical fiber is intact, it propagates light and when the fiber is damaged, the light decreases. In the case where the optical fiber is broken or destroyed or even under some conditions of shock and vibration, the light cannot propagate or propagation is decreased through the optical circuit. When a projectile strikes a target, the impact will be at a first area of the projectile. Depending on the design of the projectile, this first area will begin to crush, collapse, fragment, explode, or similar. Given the ultra-high velocity of the impact, high energies are involved and the materials at the first area of the projectile begin to transition to an indefinite and/or unpredictable state. The optical fiber in the first area is possibly deformed, then destroyed, resulting in an interruption to the light propagating through the optical fiber. The shockwave from the impact begins to travel through the projectile from the first area of impact toward the second area farther away from the impact. The velocity of light in fiber is significantly faster than even ultra-high velocity impacts of a projectile with a target. This difference in velocities allows the monitor to detect a change in the light at the second area before the shockwave reaches the second area and damages or destroys the monitor.

SUMMARY OF INVENTION

Even though certain impact sensors provide the ability to detect and report ultra-high velocity impacts, there still can be a high degree of uncertainty as to the circumstances of the impact. For example, in threat neutralization applications where the projectile is an anti-projectile projectile, also referred to as a "kill vehicle," there can be uncertainty as to whether the correct target (i.e., the threat and not something else) was struck by the projectile, or whether the threat was completely destroyed or neutralized by the impact. Existing methods of attempting to address these uncertainties include radar tracking and optical tracking of the kill vehicle and the threat, and observing the impact for proper flash intensity or other expected characteristics that would indicate that the threat has been struck and destroyed. However, these methods do not satisfactorily reduce or eliminate the uncertainties. Furthermore, due to the data latencies involved in determining whether the threat was hit and destroyed, it can be necessary to deploy multiple kill vehicles per threat, which may not be an efficient or optimal use of resources. Accordingly, aspects and embodiments are directed to impact sensors, and more particularly to a class of impact sensors for hyper-velocity impacts that are configured to spectroscopically analyze the impact to assist in identifying the target and assessing the result of the impact.

According to one embodiment a hyper-velocity impact sensor comprises an optical fiber probe configured to transmit an optical pulse generated during impact with an object, a spectroscopic analyzer configured to receive the optical pulse and produce spectral information about the optical pulse, connecting optical fiber configured to convey the optical pulse between the optical fiber probe and the spectroscopic analyzer, and at least one processor coupled to the spectroscopic analyzer and configured to receive and analyze the spectral information to determine a chemical composition of the object.

In one example the spectroscopic analyzer includes a dispersive element that spectrally disperses the optical pulse to provide dispersed light, and a photosensitive detector that receives the dispersed light and records a corresponding spectrum. The dispersive element may be a diffraction grating or a prism, for example. In one example the at least one processor is configured to receive the corresponding spectrum and to detect at least one spectral line in the corresponding spectrum, the at least one spectral line corresponding to a known chemical element or compound. The at least one processor may be further configured to classify the object based at least in part on the known chemical element or compound.

In one example the hyper-velocity impact sensor further comprises a transmitter coupled to the at least one processor. The transmitter may be configured to transmit a signal that includes a classification of the object. In another example the transmitter is configured to transmit a signal that includes identification of the known chemical element or compound.

In another example the spectroscopic analyzer includes a spectral filter that filters the optical pulse based on at least one known chemical element or compound to produce the spectral information. The spectral filter may include a gas filter, for example.

The hyper-velocity impact sensor may further comprise an optical detector, and a beamsplitter disposed at a distal end of the connecting optical fiber, a proximal end of the connecting optical fiber being connected to the optical fiber probe, the beamsplitter being configured to split the optical pulse into a first portion directed to the optical detector and a second portion directed to the spectroscopic analyzer. In one example the optical detector is configured to extract a height and a width of the optical pulse to estimate a density and a thickness of at least one material of the object.

Another embodiment is directed to a projectile including an example of the hyper-velocity impact sensor, wherein the optical fiber probe is disposed at a forward impact region of the projectile, and the spectral analyzer and the at least one processor are disposed in an aft region of the projectile. The projectile may be configured to explode, destroy with kinetic energy, embed, or pass through the object.

According to another embodiment a hyper-velocity impact sensor comprises an optical fiber probe configured to transmit an optical pulse generated during impact with an object, a beamsplitter coupled to the optical fiber and configured to split the optical pulse into a first portion and a second portion, an optical detector arranged to receive the first portion of the optical pulse, a dispersive element arranged to receive the second portion of the optical pulse and to spectrally disperse the second portion of the optical pulse to provide dispersed light, a photosensitive detector that receives the dispersed light and records corresponding spectral information about the optical pulse, and at least one processor coupled to the photosensitive detector and configured to receive and analyze the spectral information to identify at least one chemical element or compound contained in the object.

In one example the optical detector is configured to extract a height and a width of the optical pulse to estimate a density and a thickness of at least one material of the object. The dispersive element may be a diffraction grating or a prism, for example. The hyper-velocity impact sensor may further comprise a transmitter coupled to the at least one processor, the transmitter being configured to transmit a signal that includes information about the object. In one example the information about the object includes an identification of the at least one chemical element or compound contained in the object. In another example the information about the object includes a classification of the object based on the at least one chemical element or compound contained in the object. The hyper-velocity impact sensor may further comprise a connecting optical fiber coupling the beamsplitter to the optical fiber probe and configured to convey the optical pulse between the optical fiber probe and the beamsplitter.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures.

DETAILED DESCRIPTION

Figure 1:
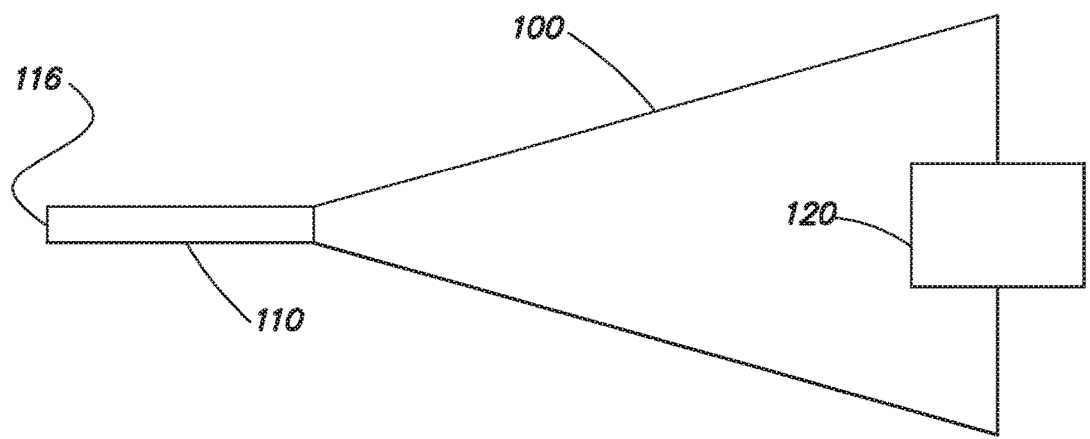
FIG. 1 is a block diagram of one example of a projectile outfitted with a sensor system including a hyper-velocity penetrating probe according to aspects of the present invention.

As discussed above, hyper-velocity impact sensors can be used to detect and report ultra-high velocity collisions between a projectile, such as a kinetic energy weapon or so-called kill vehicle, and a target. In particular, an optical fiber impact sensor can be used to detect and transmit certain information about the impact before the sensor is destroyed. However, guaranteed kill assessment of threats (i.e., determination with certainty that the threat was destroyed or neutralized) cannot be achieved using conventional approaches and technologies. Uncertainties in discrimination of threats versus other objects, and the data latencies between the time of the impact and the time at which an acceptably accurate determination can be made as to the identity of the impacted target and result of the impact (e.g., was the target destroyed) are prohibitive.

Aspects and embodiments are directed to a hyper-velocity impact sensor system that includes an optical fiber hyper-velocity penetrating probe that can be disposed on a projectile, and a detector for spectroscopically analyzing the resulting flash-generated pulse from a collision between the projectile and an impacted object. In certain examples the sensor can extract information about the impacted object, such as the density or thickness of the impacted object, as well as spectroscopic information that can be used to identify materials of the impacted object. In ultra-high or hyper-velocity impacts, namely impacts at speeds of greater than 1,000 m/s and up to approximately 15,000 m/s, as the mass of the colliding objects is consumed, it changes state from a solid material into a pulse of energy in the form of a flash of light and heat. Information characterizing the velocity of impact and the density and thickness of the impact objects is encoded into that pulse of energy. The pulse height provides information about impact velocity and the density of the impacted object. The pulse width provides information about impact velocity and the thickness of the impacted object. Spectroscopic analysis of the pulse can reveal further information, such as chemical composition, that can be used to identify particular materials in the impacted object. As discussed in more detail below, the spectroscopic analysis can be performed during the collision before the sensor system is destroyed or rendered inoperable, and the resulting spectroscopic information can be used to identify the impacted object. In certain embodiments, the spectroscopic information can be transmitted to a base station or to other kill vehicles, allowing for reliable kill assessment and potential re-direction of following kill vehicles to other potential targets.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Referring FIG. 1, there is illustrated a schematic block diagram of one example of a projectile outfitted with a hyper-velocity impact sensor system, according to certain embodiments. The projectile itself may be configured to explode, destroy with kinetic energy, embed in or pass through an object with a relative closing velocity greater than 1,000 m/s up to about 15,000 m/s. As shown in FIG. 1, the projectile 100 includes a probe 110 that extends forward of the projectile, such that a front end or tip 116 of the probe will first impact an object, and is in communication with electronics 120 aft of the projectile. The electronics 120 reads out outputs from the probe 110 as the probe (and impacted object) are consumed at impact, and transmits information to a remote location before the electronics are consumed. In certain examples in which the projectile 100 is a kill vehicle, the probe 110 can be mounted on as forward section of the kill vehicle, such as the sunshade, for example. The probe 110 and electronics 120 together form one example of a hyper-velocity impact sensor system.

Figure 2:
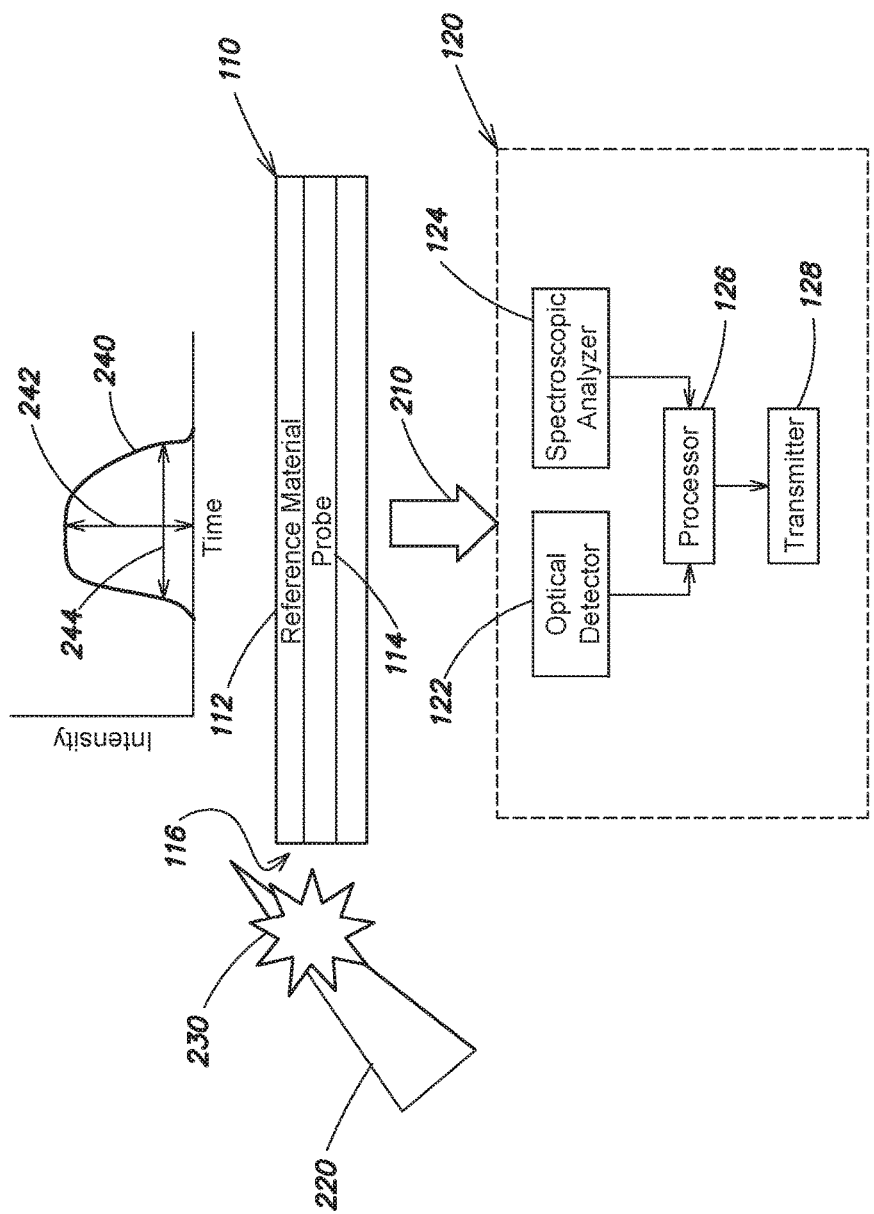
FIG. 2 is a block diagram of one example of a hyper-velocity impact sensor system according to aspects of the present invention.

FIG. 2 is a block diagram of one example of a hyper-velocity impact sensor system according to certain embodiments. Referring to FIG. 2, in one embodiment, the probe 110 includes a reference material 112, and an optical fiber 114 embedded along the length of the reference material. The optical fiber 114 acts as a probe sensor. The optical fiber 114 may be jacketed inside another material for stiffness and protection. As discussed above, the probe 110 preferably can be arranged on a projectile such that when collision between the projectile and a target object occurs, the probe strikes the target object in an "end-on" direction; in other words, the tip 116 strikes the target object first. This arrangement of the probe 110 provides the longest time during which to perform the sensing discussed below. The electronics 120 includes an optical detector 122 configured to detect and read out a probe output 210, a spectroscopic analyzer 124 configured to detect and spectroscopically analyze the probe output 210, and at least one processor 126 configured to process the probe output 210 based on information provided by the optical detector 122 and the spectroscopic analyzer 124 to provide information about an impacted object 220. For example, the at least one processor 126 may classify the impacted object 220 as one of the known objects. The at least one processor 126 may include one or more processors that can be positioned with the optical detector 122 or spectroscopic analyzer 124, respectively, or located remotely to receive transmission of the probe output 210. The electronics 120 further includes a transmitter 128 coupled to the at least one processor 126 and configured to transmit information regarding the impacted object 220 obtained from processing the probe output 210 to a remote location, such as a ground-based or air-based station or another projectile.

At ultra-high or hyper velocities, impact of the projectile and probe 110 with the impacted object 220 consumes both the reference material 112 and object material at the point of impact. The denser or thicker the impacted object 220 the more of the material and probe 110 that will be consumed. This consumption of material, changing its state from a solid to energy, produces a plasma flash 230 and heat, which generate an optical pulse of energy 240 that travels along the optical fiber 114. The pulse height 242 is proportional to the kinetic energy of the impact, which provides information about the impact velocity and the density of the impacted object 220. The pulse width 244 is proportional to the time the probe 110 travels through the impacted object 220, which provides further information about the impact velocity and information about the thickness of the impacted object. Knowing the properties of the reference material 112 and the optical fiber 114, the data can be processed to extract density and thickness information of the impacted object 220, as discussed further below. The optical pulse 240 further includes spectral information that is dependent on the materials being consumed (both of the probe 110 and the impacted object 220). As discussed further below, the spectroscopic analyzer 124 includes a dispersive element that spectrally disperses the optical pulse 240 and a detector that images the resulting spectra. The at least one processor 126 can be configured to analyze the spectra and/or capture information from the spectral analyzer detector to provide information about the chemical composition of the impacted target 220.

In one embodiment, the optical fiber 114 extends along the length of the reference material 112 from a forward impact area to a rear area where it is coupled to the electronics 120. The reference material 112 and the optical fiber 114 can be configured such that varying and known amounts of the material are consumed during impact with different objects of known density at closing velocities within a specified range to generate probe outputs 210 indicative of the amount and rate of material consumed. The optical detector 122, which can include analog or digital circuitry, reads out a temporal sequence of one or more probe outputs 210 that encode the velocity, density and thickness parameters. The at least one processor 126 processes the outputs from the optical detector 122 to extract (implicitly or explicitly) parameters by which to characterize and/or classify the impacted object 220. For example, the at least one processor 126 may explicitly calculate values for the density and/or thickness. Alternately, the at least one processor 126 may implement a set of matched filters, each designed based on the density and thickness properties of a known object, thereby implicitly calculating the parameters. In certain examples the at least one processor 126 can use the estimate of actual impact velocity to compensate for any variances to an expected impact velocity.

The reference material 112 may be an independent element of just the hyper-velocity impact sensor system or may be integrated with the projectile 100. The reference material can be selected and configured to match the "dynamic range" of expected impacts with different objects within a specified range of relative impact velocities. The density and thickness (total mass) of impacted objects may vary widely or little. For example, in a ballistic missile defense system a kill vehicle may target and impact a balloon countermeasure, debris, or the hardened nuclear warhead; each of these objects having a very different mass signature. In other applications, a target object may comprise only objects whose density and thickness are similar. Accordingly, in certain examples the reference material 112 can be selected to have an appropriate density and total mass such that in the expected velocity range, the thinnest/lightest potential target object consumes sufficient material to produce a measurable output and the thickest/densest potential target objects consume different amounts of material to produce differentiated outputs. The reference material 112 can be also be selected to comprise one or more materials having a chemical composition that is unlikely to mask the spectral signature of certain materials anticipated to be part of particular target objects, as discussed further below. The amount of mass consumed, and the rate of consumption, are calibrated to object density and thickness and stored in the at least one processor 126. Possible reference materials may include, but are not limited to, various composites, various ceramics or glasses, various metals such as steel, titanium, depleted uranium, etc., or the optical fiber material of the optical fiber 114.

Figure 3:
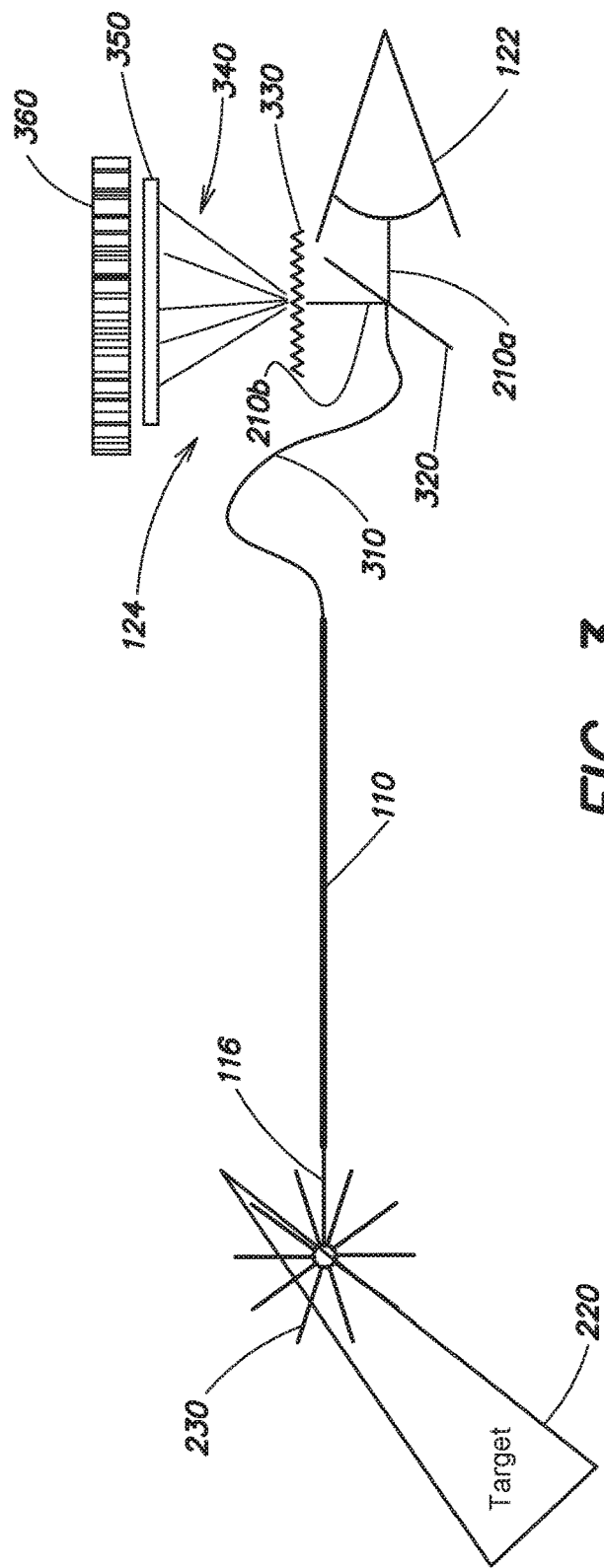
FIG. 3 is a diagram showing further aspects of the hyper-velocity impact sensor system of FIG. 2, according to aspects of the present invention.

As discussed above, the probe sensor 114 must generate and convey the probe outputs 210 very quickly to the electronics 120 to stay in front of the shock wave produced by the optical pulse 230 before it consumes the electronics 120 or otherwise renders the electronics inoperable. Referring to FIG. 3, according to certain embodiments, the probe 110 is coupled to the electronics aft by a connecting optical fiber 310. At impact with the target object 220, at least some of the reference material 112 and the optical fiber 114 towards the tip 116 of the probe 110 will be consumed. As discussed above, the plasma 230 formed and heat generated in the impact will generate the optical pulse 240 both inside and outside the optical fiber 114. The optical pulse 240 includes spectral information that is dependent on the materials being consumed, and those materials will include materials of both the probe 110 and the impacted object 220. The pulse inside the fiber can be coupled into the connecting fiber 310 and will travel down the probe 110 and connecting fiber 310 at approximately two-thirds the speed of light toward the electronics 120. A beamsplitter 320 is used to separate the probe output 210 into two detection paths. A first portion 210a of the probe output is directed to the optical detector 122 where the pulse height 242 and pulse width 244 can be read out as discussed above. The optical detector 122 may extract the height and width parameters directly or may sample the pulse at a sufficiently high rate to capture the height and width information. A second portion 210b of the probe output is directed to the spectroscopic analyzer 124 for spectral analysis. In the illustrated example the first portion 210a of the probe output is transmitted through the beamsplitter 320 to the optical detector 122 and the second portion 210b is reflected by the beamsplitter to the spectroscopic analyzer 124; however, it will be readily apparent to those skilled in the art that the opposite arrangement can be implemented.

The spectroscopic analyzer 124 includes a dispersive element 330 that receives the second portion 210b of the probe output 210b and spectrally disperses the pulse into its spectral constituents, as indicated at 340. The spectroscopic analyzer 124 further includes a photosensitive detector 350 that receives the spectrally dispersed light and produces spectral lines or an image of the spectrum 360. The dispersive element 330 may be a diffraction grating or a prism, for example. In other examples the dispersive element 330 can be replaced with a spectral filter, such as a gas filter (e.g., a gas containing a particular element or compound as can be used for gas filter correlation spectroscopic methods) or a dielectric filter (e.g., a thin film dielectric bandpass filter). The photosensitive detector 350 can include a linear charge-coupled device (CCD) array, a linear avalanche photodiode (APD), a line scanning array, or another type of optical array that is used to record the spectral information.

Analysis of the recorded spectral information, for example, by the at least one processor 126, can determine types of materials involved in the collision, which in turn can be used to identify or classify the impacted object 220. For example, strong spectral lines from each of the elements being consumed and plasma-ized can be used to identify the materials present in the impacted object 220, thereby identifying its chemical composition. In at least certain applications in which expected targets have a non-uniform composition (e.g., an explosive threat may include an outer casing with the explosive materials contained inside the casing), the spectra 360 will evolve over the time of the collision as the probe 110 penetrates different materials as it penetrates the impacted object 220. The spectroscopic analyzer 124 can be configured to continuously record and analyze spectra, thereby providing information as to the different materials encountered as the probe 110 penetrates the impacted object 220, until it is destroyed by the impact.

As discussed above, there is only a very short time, for example, on the order of a few milliseconds, available in which to record the spectra 360 and perform the spectral analysis before the probe 110 and electronics 120 are destroyed by the impact. Accordingly, in certain examples, the at least one processor 126 is configured to detect particular lines in the spectra 360 that would indicate the presence of particular materials of interest. For example, the at least one processor can be programmed to look for the spectral lines associated with one or more chemical elements/compounds that are expected to be present within a certain type of target. This programming may differ among different applications. For example, if the projectile 100 is a kill vehicle deployed to neutralize a chemical, nuclear, or biological weapon, the at least one processor 126 can be configured to detect specific spectral lines associated with materials known to be used in these types of targets. In certain examples the at least one processor 126 can be configured to identify of classify the impacted object 220 based on analysis of the recorded spectra 360, and transmit this information to a remote location via the transmitter 128. In other examples, the at least one processor 126 and transmitter 128 can be configured to transmit information about the spectra 360 (e.g., information identifying elements or compounds corresponding to strong spectral lines, or even a digital representation of the spectrum itself), and identification/classification of the impacted object 220 can be performed remotely based on the received information.

Thus, aspects and embodiments provide an optical fiber-based hyper-velocity penetrating probe and associated electronics that can be used to detect and analyze optical pulses generated during high-velocity impacts. The system can be used to obtain spectral information, as well as density and thickness information about the materials being consumed during the impact. In particular, as discussed above, spectroscopic evaluation of the projectile/target collision allows real time determination of the chemical nature of the impacted object 220 as it is destroyed. It also allows monitoring of the evolution of the spectrum over the short time of the collision. Knowing the spectroscopic nature of the optical pulse 240 allows analysis during the collision of what has actually been collided with. This greatly reduces uncertainty as to the nature of the impacted object, for example reducing uncertainty as to whether a designated target was hit, or something else was hit. In anti-threat applications, greater certainty as to the identity of the impacted object 220 reduces the need for as many follow-on kill vehicles (thereby saving resources) and allows faster redirection of additional kill vehicles to other potential targets.

Embodiments and configurations of the hyper-velocity penetrating probe system disclosed herein have utility in a wide variety of applications. For example, as discussed above, in anti-threat applications, the thickness, density, and spectroscopic information obtained can be used to classify the type of threat destroyed, including various classes of nuclear, dirty, chemical, biological, and conventional weapons. The techniques disclosed herein can also be used to provide the ability to determine mineral content in asteroids and comets for astro-mining or exploration applications, for example. The hyper-velocity penetrating probe system can also be configured to provide any or all of the density, thickness, and spectroscopic information, and is not limited in application to providing all three classes of information. For example, in certain embodiments, the electronics 120 can include only the spectroscopic analyzer 124 without the optical detector 122. In this configuration, the beamsplitter 320 can be omitted.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A hyper-velocity impact sensor comprising:
    an optical fiber probe configured to transmit an optical pulse generated during impact with an object;
    a spectroscopic analyzer configured to receive the optical pulse and produce spectral information about the optical pulse;
    a connecting optical fiber configured to convey the optical pulse between the optical fiber probe and the spectroscopic analyzer; and
    at least one processor coupled to the spectroscopic analyzer and configured to receive and analyze the spectral information to determine a chemical composition of the object.

2. The hyper-velocity impact sensor of claim 1 wherein the spectroscopic analyzer includes:
    a dispersive element that spectrally disperses the optical pulse to provide dispersed light; and
    a photosensitive detector that receives the dispersed light and records a corresponding spectrum.

3. The hyper-velocity impact sensor of claim 2 wherein the dispersive element is a diffraction grating.

4. The hyper-velocity impact sensor of claim 2 wherein the dispersive element is a prism.

5. The hyper-velocity impact sensor of claim 2 wherein the at least one processor is configured to receive the corresponding spectrum and to detect at least one spectral line in the corresponding spectrum, the at least one spectral line corresponding to a known chemical element or compound.

6. The hyper-velocity impact sensor of claim 5 wherein the at least one processor is configured to classify the object based at least in part on the known chemical element or compound.

7. The hyper-velocity impact sensor of claim 6 further comprising a transmitter coupled to the at least one processor, the transmitter being configured to transmit a signal that includes a classification of the object.

8. The hyper-velocity impact sensor of claim 5 further comprising a transmitter coupled to the at least one processor, the transmitter being configured to transmit a signal that includes identification of the known chemical element or compound.

9. The hyper-velocity impact sensor of claim 1 wherein the spectroscopic analyzer includes a spectral filter that filters the optical pulse based on at least one known chemical element or compound to produce the spectral information.

10. The hyper-velocity impact sensor of claim 9 wherein the spectral filter includes a gas filter.

11. The hyper-velocity impact sensor of claim 1 further comprising:
    an optical detector; and
    a beamsplitter disposed at a distal end of the connecting optical fiber, a proximal end of the connecting optical fiber being connected to the optical fiber probe, the beamsplitter being configured to split the optical pulse into a first portion directed to the optical detector and a second portion directed to the spectroscopic analyzer.

12. The hyper-velocity impact sensor of claim 11 wherein the optical detector is configured to extract a height and a width of the optical pulse to estimate a density and a thickness of at least one material of the object.

13. A projectile including the hyper-velocity impact sensor of claim 1, wherein the optical fiber probe is disposed at a forward impact region of the projectile, and the spectral analyzer and the at least one processor are disposed in an aft region of the projectile.

14. The projectile of claim 13 wherein the projectile is configured to explode, destroy with kinetic energy, embed, or pass through the object.

15. A hyper-velocity impact sensor comprising:
    an optical fiber probe configured to transmit an optical pulse generated during impact with an object;
    a beamsplitter coupled to the optical fiber and configured to split the optical pulse into a first portion and a second portion;
    an optical detector arranged to receive the first portion of the optical pulse;
    a dispersive element arranged to receive the second portion of the optical pulse and to spectrally disperse the second portion of the optical pulse to provide dispersed light;
    a photosensitive detector that receives the dispersed light and records corresponding spectral information about the optical pulse; and
    at least one processor coupled to the photosensitive detector and configured to receive and analyze the spectral information to identify at least one chemical element or compound contained in the object.

16. The hyper-velocity impact sensor of claim 15 wherein the optical detector is configured to extract a height and a width of the optical pulse to estimate a density and a thickness of at least one material of the object.

17. The hyper-velocity impact sensor of claim 15 wherein the dispersive element is one of a diffraction grating and a prism.

18. The hyper-velocity impact sensor of claim 15 further comprising a transmitter coupled to the at least one processor, the transmitter being configured to transmit a signal that includes information about the object.

19. The hyper-velocity impact sensor of claim 18 wherein the information about the object includes at least one of an identification of the at least one chemical element or compound contained in the object, and a classification of the object based on the at least one chemical element or compound contained in the object.

20. The hyper-velocity impact sensor of claim 15 further comprising a connecting optical fiber coupling the beamsplitter to the optical fiber probe and configured to convey the optical pulse between the optical fiber probe and the beamsplitter.

* * * * *